United States Patent [19]

Coneys

[11] Patent Number: 4,657,024

[45] Date of Patent: Apr. 14, 1987

[54] MEDICAL-SURGICAL CATHETER

[75] Inventor: Thomas A. Coneys, Mendham, N.J.

[73] Assignee: Teleflex Incorporated, Limerick, Pa.

[21] Appl. No.: 767,098

[22] Filed: Aug. 19, 1985

Related U.S. Application Data

[63] Continuation of Ser. No. 560,273, Dec. 12, 1983, abandoned, and a continuation of Ser. No. 383,980, Jun. 1, 1982, which is a continuation of Ser. No. 118,411, Feb. 4, 1980, abandoned.

[51] Int. Cl.$^4$ ............................................. A61M 25/00
[52] U.S. Cl. .................................. 128/658; 604/280; 138/118
[58] Field of Search .................. 128/658, DIG. 21; 604/280, 264; 138/118; 428/36

[56] References Cited

U.S. PATENT DOCUMENTS

| | | | |
|---|---|---|---|
| 2,857,915 | 10/1958 | Sheridan | 604/658 |
| 3,070,132 | 12/1962 | Sheridan | 604/280 |
| 3,529,633 | 9/1970 | Vaillancourt | 604/280 |
| 3,605,750 | 9/1971 | Sheridan et al. | 604/280 X |
| 3,608,555 | 9/1971 | Greyson | 128/658 |
| 4,027,659 | 6/1977 | Slinghuff | 604/280 X |
| 4,277,432 | 7/1981 | Woinowski | |

Primary Examiner—Stephen C. Pellegrino
Attorney, Agent, or Firm—Weiser & Stapler

[57] ABSTRACT

A medical-surgical catheter comprising an extruded tube of flexible material including a plastic material transparent to X-ray radiation and defining the entire interior and exterior surfaces of the tube to provide smooth surfaces of low coefficient of friction and a integrally extruded radiopaque layer completely embedded within and surrounded by the plastic material and extending along the tube between the ends thereof. The radiopaque layer comprises a blended mixture of radiopaque material and the plastic material with the blended mixture of the layer completely surrounded by a pure composition of the plastic material. The radiopaque layer may comprise an annular tube with an outer annular layer of the plastic material and an inner annular layer of the plastic material or the radiopaque layer may comprise a pair of diametrically opposed strips or the radiopaque layer may comprise a plurality of circumferentially spaced strips extending in a helical path along the tube.

18 Claims, 4 Drawing Figures

MEDICAL-SURGICAL CATHETER

This is a continuation of application Ser. No. 560,273, filed Dec. 12, 1983, now abandoned, and a continuation of application Ser. No. 383,980, filed June 1, 1982, which is a continuation of application Ser. No. 118,411 filed Feb. 4, 1980, now abandoned.

BACKGROUND OF THE INVENTION (1) Field of the Invention

The subject invention relates to a medicalsurgical tube such as that used in a catheter. The term "catheter" as used herein means any medical-surgical tube which includes a proximal end, a distal end and a longitudinal bore extending between the ends with the distal end having an opening. The catheter tubes are designed for insertion into some tissue, organ, cavity as, for example, a vascular or arterial branch, or the like, in a patient to serve as a channel for removing fluids from or introducing fluids into the tissue, organ, cavity, or the like, within the patient. Such catheters are frequently combined with syringes, valves, fluid traps or other units in creating assemblies required for the particular medical or clinical procedure being applied to the patient.

(2) Description of the Prior Art

Extensive use is being made of disposable catheters designed for single patient and single use. Such disposable catheters are most commonly produced by an extrusion of waterproof and inert plastic material which is nontoxic, nonabsorbitive and resistant to attack or deterioration by fluids of body tissue into which the catheter may be inserted in the course of a surgical or clinical procedure. In many surgical or clinical procedures, it is important to be able to determine the location or position of the catheter within the body of the patient into which it has been inserted. Furthermore, in some situations a tube inserted into the body of a patient may break off and it is imperative that a broken-off piece of tube be locatable. X-ray observation is a convenient method of making this position determination, but the usual plastic material from which catheters are made is not X-ray opaque, i.e., radiopaque. Accordingly, several catheter constructions have been devised in order to permit the body position of the catheter to be determined by X-ray observation. Such constructions include a radiopaque material combined or mixed with the plastic material of the catheter. However, the radiopaque material is frequently chemically reactive with body tissues and/or is rough or coarse and when exposed on the exterior of the catheter provides a relatively high coefficient of friction which causes irritation or impairs the insertion of the catheter into a tissue and when exposed to the interior of the tube provides a rough surface which frequently causes bruising of the blood which may, in turn, cause clotting. In some constructions the amount of radiopaque material is not sufficient for good detection of the placement of the catheter in all locations. If the amount of radiopaque material is increased for detection deep within the body, it may be unacceptable because of its roughness and/or because of it being too reactive. If the radiopaque material is sufficient for adequate radiopacity, the surface roughness and chemical reactivity is a problem and if reduced there may not be sufficient radiopacity.

SUMMARY OF THE INVENTION

The subject invention provides a medicalsurgical tube comprising an extruded tube of flexible material including a plastic material transparent to X-ray radiation and defining the entire interior and exterior surfaces of the tube to provide smooth surfaces of a low coefficient of friction and a radiopaque layer completely embedded within and surrounded by the plastic material and extending along the tube between the ends thereof so as to provide an improved catheter overcoming many of the disadvantages of the prior art catheters.

PRIOR ART STATEMENT

An early construction of a catheter which is radiopague is illustrated in U.S. Pat. No. 2,212,334, granted Aug. 20, 1940 to George W. Wallerich, wherein the catheter is made by first mixing bismuth powder with an appropriate cellulosic material and extruding the plastic compound. The radiopaque or X-ray opaque material is rough or coarse and is exposed to the inner and outer surfaces of the tube whereby the outer surface may be irritable to the skin tissues when inserted and the inner surfaces may cause bruising of the blood.

Another construction is shown in U.S. Pat. No. 2,857,915, granted Oct. 28, 1958 to David S. Sheridan, wherein a thin strip of radiopaque material is disposed in the outer circumference of the plastic tube. Again, the roughness of the radiopaque material of the strip is exposed to the outer surface of the catheter and, further, the amount of radiopaque material in the strip is not sufficient for many X-ray purposes. A further example of a catheter utilizing a thin strip of opaque material exposed to the outer surface of the catheter is illustrated in U.S. Pat. No. 3,295,527, granted Jan. 3, 1967 to Ralph D. Alley et al.

U.S. Pat. No. 3,529,633 granted Sept. 22, 1970 to Vincent L. Vaillancourt, like U.S. Pat. No. 2,212,334 discussed above, discloses a catheter with a portion of the circumference including plastic filled with a radiopaque material but differs from the aforementioned patent in that the remainder of the circumference of the tube consists of unfilled plastic. Again, however, the portion of the circumference of the tube having plastic filled with the radiopaque material has a relatively rough surface.

In another construction illustrated in U.S. Pat. No. 3,605,750, granted Sept. 20, 1971 to David S. Sheridan et al, there is disclosed a plastic tube with a bore extending longitudinally into the tube with short filaments of radiopaque material inserted into the bores. This construction provides a tube with a completely different structural integrity than the subject invention. Further, it is very difficult to place the radiopaque filaments in the bore and it is difficult to form the bore in the tube for receiving the spaced filaments.

In U.S. Pat. No. 3,618,614, granted Nov. 9, 1971 to Vincent J. Flynn, there is disclosed a catheter construction wherein the radiopaque material is in a concentric annular tube either on the interior or the exterior of the plastic tube. The roughness of the radiopaque material either exteriorly or interiorly of the catheter is undesirable.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

Figure 1:
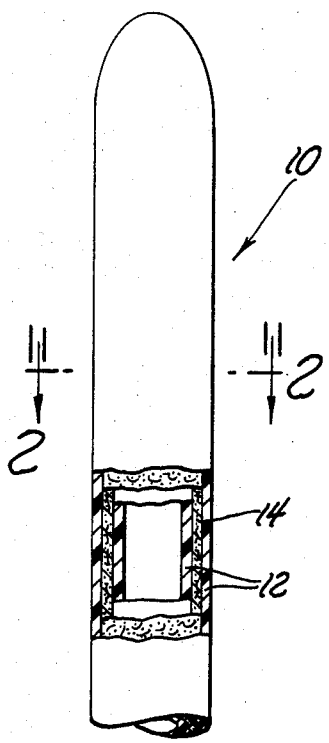
FIG. 1 is a view partially broken away and in cross section of the distal end of a medical-surgical catheter constructed in accordance with the subject invention.
Figure 2:
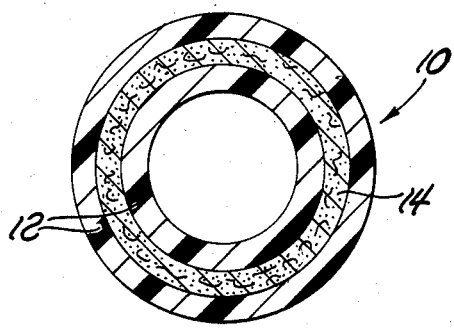
FIG. 2 is an enlarged cross-sectional view taken substantially along line 2—2 of FIG. 1.

A medical-surgical catheter constructed in accordance with the subject invention is generally shown at 10 in FIGS. 1 and 2. The catheter includes an extruded tube of flexible material. The flexible material includes a plastic material transparent to X-ray radiation and defining the entire exterior and interior surfaces of the tube to provide smooth surfaces of a low coefficient of friction. In other words, the plastic material 12 defines the inner tubular bore surface as well as the exterior surface of the tube. Further, the flexible material includes an integrally extruded radiopaque layer 14 completely embedded within and surrounded by the plastic material 12 and extending along the tube between the ends thereof. The end of the tube illustrated is usually sharp and exposes the central bore through an opening (not shown) for the passage of fluid. The plastic material 12 is preferably polyfluorinated ethylenepropylene but may be one of various alternative thermoplastic materials.

The radiopaque layer 14 comprises a blended mixture of radiopaque material and a binder material. The binder material and the plastic material are compatible for bonding and are bonded together. The binder material may be the same plastic material as the virgin or pure plastic material 12. In other words, the radiopaque layer 14 is a homogeneous mixture of a radiopaque material and the same kind of plastic as the pure plastic 12. The blended mixture of the layer 14 is completely surrounded by a pure composition of the plastic material 12. The radiopaque material is more coarse and abrasive than the plastic material defining the portions 12. The radiopaque material may be barium sulfate, bismuth trioxide, bismuth subcarbonate or tungsten powder or one of various other alternative radiopaque materials. By way of example, the blended mixture of the radiopaque material defining the layer 14 may include between twenty percent (20%) and thirty percent (30%) fluorinated ethylenepropylene with the remaining seventy percent (70%) to eighty percent (80%) being one of the radiopaque materials identified above. The blended mixture is extruded simultaneously with the pure composition of the fluorinated ethylene-propylene 12 to define the catheter. Further, the radiopaque material preferably comprises between twelve percent (12%) and twenty-five percent (25%) of the total weight of the material making up the tube. In other words, the amount of radiopaque material in the blend making up the layer 14 comprises between twelve percent (12%) and twenty-five percent (25%) of the total material making up the tube. The radiopaque layer 14 comprises an annular tube with an outer annular layer of the plastic material thereabout to define the exterior surface and an inner annular layer of plastic material therewithin to define the interior surface. In other words, as viewed in cross section the radiopaque layer 14 is arcuate and extends completely about the circumference of the tube.

DESCRIPTION OF THE ALTERNATIVE EMBODIMENTS

Figure 3:
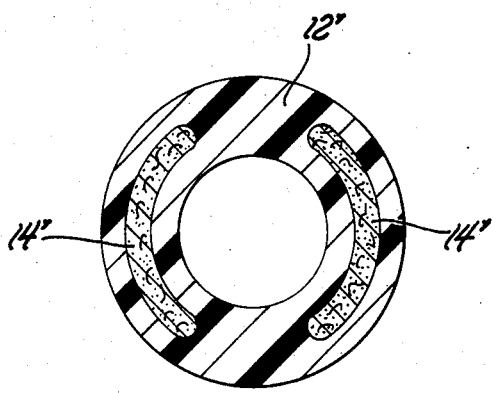
FIG. 3 is a cross-sectional view similar to FIG. 2 but showing an alternative embodiment.

FIG. 3 illustrates an alternative embodiment of the catheter of the subject invention wherein the pure plastic material 12' completely encapsulates and surrounds a pair of diametrically opposed strips 14' which define the radiopaque layer. The radiopaque layer defined by the strips 14' also comprises a blend and radiopaque material and a plastic material the same as the plastic material 12'. Each of the strips 14' when viewed in cross section are arcuate to extend about a portion of the circumference of the tubular member so that the remaining portion of the circumference of the tube is made up solely of the plastic material 12' which, as in all embodiments, may be transparent whereby flow through the tube may be viewed visually.

Figure 4:
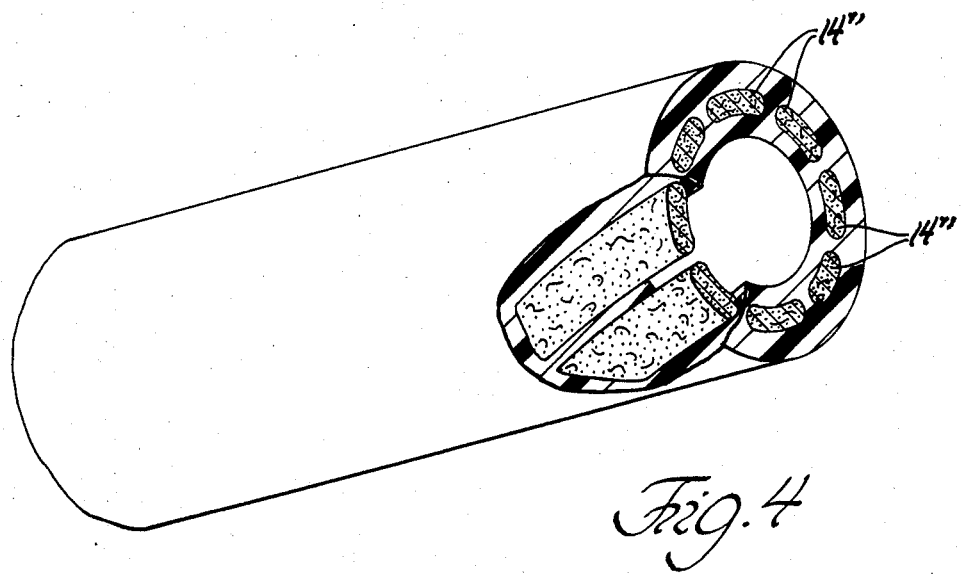
FIG. 4 is a fragmentary perspective view partially broken away and in cross section showing yet another embodiment.

Yet another embodiment is illustrated in FIG. 4 wherein the radiopaque layer is made up of a plurality of strips 14" spaced from one another circumferentially about the tube and extending in a helical path about the tube as the strips extend along the tube. The strips 14" are also made up of a blend of the radiopaque material and the plastic of the type in which the strips 14" are completely embedded and surrounded.

In accordance with the subject invention the radiopaque layer (the blend of the pure plastic and the radiopaque material) is completely embedded and surrounded on all surfaces by the pure composition of the plastic material thereby providing a catheter having surfaces with a low coefficient of friction yet providing a catheter having a very high concentration of the radiopaque material and chemical inertness which has been unattainable in the prior constructions.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

The embodiment of the invention in which an exclusive property or privilege is claimed are defined as follows:

1. An improved flexible medical-surgical tube which has a circumferential exterior wall with a smooth surface for the entire wall, which wall defines an outer annular layer within the tube, which tube comprises a thermoplastic material, which material defines a longitudinal region integrally coextruded through the thermoplastic material, which region extends continuously throughout the entire length of the tube, which longitudinal thermoplastic region consists of a homogeneous blend of thermo-plastic and radiopaque material which is homogeneously dispersed throughout said thermoplastic longitudinal region, said region being completely embedded in the thermoplastic material throughout the entire length of the tube.

2. The improved flexible medical-surgical tube of claim 1 wherein the smooth surface of the exterior circumferential wall is protrusion-free.

3. The improved flexible medical-surgical tube of claim 1 wherein the exterior circumferential wall is protrusion-free for the entire length and circumference of the tube.

4. The improved flexible medical-surgical tube of claim 1 wherein the thermoplastic material in which the longitudinal region is completely embedded is constituted solely of thermoplastic material.

5. The improved flexible medical-surgical tube of claim 1 wherein in the region, the amount of thermoplastic to radiopaque material is in the range from 20 to 30% and in the range from 80 to 70% by weight, respectively.

6. The improved flexible flexible medical-surgical tube of claim 1 which has an exterior wall which has a smooth surface and is protrusion-free, which tube has a plurality of longitudinal regions each being completely embedded in the thermoplastic material throughout the entire length of the tube.

7. The improved flexible medical-surgical tube of claim 6 wherein the thermoplastic longitudinal regions are also elongated radially within the thermoplastic material.

8. The improved flexible medical-surgical tube of claim 6 wherein the regions are also arcuate and extend circumferentially for a portion within the thermoplastic material.

9. The improved flexible medical-surgical tube of claim 6 wherein the plurality of longitudinal regions completely embedded in the thermoplastic material number from 2 to 8 regions.

10. The improved flexible medical-surgical tube of claim 6 wherein the longitudinal regions completely embedded in the thermoplastic material are spaced from one another circumferentially and extend in a helical path within the thermoplastic material of the tube.

11. The improved flexible medical-surgical tube of claim 6 wherein in the region, the amount of thermoplastic to radiopaque material is in the range from 20 to 30% and in the range from 80 to 70% by weight, respectively.

12. The improved flexible medical-surgical tube of claim 6 wherein the thermoplastic material is a virgin thermoplastic.

13. The improved flexible medical-surgical tube of claim 11 wherein the thermoplastic material is a virgin thermoplastic.

14. The improved flexible medical-surgical tube of claim 13 wherein the virgin thermoplastic is free of radiopaque spots, whereby the outer annular layer is of a continuous homogeneous constitution throughout.

15. An improved flexible medical-surgical tube which tube consists of a thermoplastic material which tube has a circumferential exterior wall which has a smooth, protusion-free surface for the entire length and circumference of the tube, which material defines a plurality of longitudinal regions which each extend uninterruptedly throughout the entire length of the tube, which longitudinal regions consist throughout of a homogeneous blend of thermoplastic material and a radiopaque material homogeneously dispersed throughout said thermoplastic region and said regions being completely embedded in the thermoplastic material through the entire length of the tube.

16. The improved flexible medical-surgical tube of claim 15 wherein the radiopaque material of the blend constitutes from about 12 to about 25 weight percent of the total weight of the thermoplastic material making up the medical-surgical tube.

17. The improved flexible medical-surgical tube of claim 15 wherein the circumferential smooth, protrusion-free exterior wall defines an outer annular layer of thermoplastic material which is a virgin thermoplastic which is free of radiopaque spots, whereby the outer annular layer is of an overall continuous homogeneous constitution.

18. The improved flexible medical-surgical tube of claim 17 wherein the radiopaque material of the blend constitutes from about 12 to about 25 weight percent of the total weight of the thermoplastic material making up the medical-surgical tube.

* * * * *